US010107761B2

(12) United States Patent
Shmarev et al.

(10) Patent No.: US 10,107,761 B2
(45) Date of Patent: Oct. 23, 2018

(54) METHOD AND DEVICE FOR FOCUSING IN AN INSPECTION SYSTEM

(71) Applicants: ASML NETHERLANDS B.V., Veldhoven (NL); ASML HOLDING N.V., Veldhoven (NL)

(72) Inventors: Yevgeniy Konstantinovich Shmarev, Lagrangeville, NY (US); Stanislav Smirnov, Danbury, CT (US); Chien-Hung Tseng, Wilton, CT (US); Armand Eugene Albert Koolen, Nuth (NL)

(73) Assignees: ASML NETHERLANDS B.V., Veldhoven (NL); ASML HOLDING N.V., Veldhoven (NL)

( * ) Notice: Subject to any disclaimer, the term of this patent is extended or adjusted under 35 U.S.C. 154(b) by 0 days.

(21) Appl. No.: 15/387,610

(22) Filed: Dec. 21, 2016

(65) Prior Publication Data
US 2017/0191944 A1  Jul. 6, 2017

Related U.S. Application Data
(60) Provisional application No. 62/273,982, filed on Dec. 31, 2015.

(51) Int. Cl.
*G01B 11/26* (2006.01)
*G01N 21/88* (2006.01)
(Continued)

(52) U.S. Cl.
CPC ..... *G01N 21/8806* (2013.01); *G01N 21/9501* (2013.01); *G01N 21/956* (2013.01);
(Continued)

(58) Field of Classification Search
CPC ........... G01N 21/9501; G01N 21/8806; G01N 2021/95676; G01N 21/956;
(Continued)

(56) References Cited

U.S. PATENT DOCUMENTS

| 5,304,810 A * | 4/1994 | Amos | G01N 21/6458 250/349 |
|---|---|---|---|
| 7,561,282 B1 | 7/2009 | Widmann | |

(Continued)

FOREIGN PATENT DOCUMENTS

| CN | 101226344 | 7/2008 |
|---|---|---|
| JP | 08-213306 | 8/1996 |

(Continued)

OTHER PUBLICATIONS

International Search Report and Written Opinion dated Feb. 27, 2017 in corresponding International Patent Application No. PCT/EP2016/079798.

(Continued)

*Primary Examiner* — Michael P Stafira
(74) *Attorney, Agent, or Firm* — Pillsbury Winthrop Shaw Pittman LLP

(57) ABSTRACT

An inspection apparatus including: a substrate holder configured to hold a substrate; an aperture device; and an optical system configured to direct a first measurement beam of radiation onto the substrate, the first measurement beam having a first intensity distribution, and configured to direct a second focusing beam of radiation onto the substrate at a same time as the first measurement beam is directed on the substrate, the second focusing beam having a second intensity distribution, wherein at least part of the second intensity distribution is spatially separated from the first intensity distribution at least at the substrate and/or the aperture device.

22 Claims, 11 Drawing Sheets

(51) Int. Cl.
*G01N 21/95* (2006.01)
*G01N 21/956* (2006.01)
*G03F 7/20* (2006.01)

(52) U.S. Cl.
CPC ...... *G03F 7/70625* (2013.01); *G03F 7/70641* (2013.01); *G01N 2021/8822* (2013.01); *G01N 2021/95676* (2013.01); *G01N 2201/0638* (2013.01)

(58) Field of Classification Search
CPC ..... G01N 21/95607; G01N 2021/8825; G01N 21/94; G01N 2021/479; G01N 21/95623; G01N 2201/06113; G01N 2201/10; G01N 2021/9563; G01N 2201/01
See application file for complete search history.

(56) References Cited

U.S. PATENT DOCUMENTS

| | | | |
|---|---|---|---|
| 7,957,066 B2* | 6/2011 | Armstrong | G02B 17/0812 356/237.2 |
| 8,411,287 B2 | 4/2013 | Smilde et al. | |
| 8,867,020 B2 | 10/2014 | Smilde et al. | |
| 9,081,303 B2 | 7/2015 | Cramer et al. | |
| 9,594,299 B2 | 3/2017 | Hinnen et al. | |
| 2008/0297783 A1* | 12/2008 | Urano | G01N 21/9501 356/237.5 |
| 2011/0027704 A1 | 2/2011 | Cramer et al. | |
| 2011/0043791 A1 | 2/2011 | Smilde et al. | |
| 2012/0242970 A1 | 9/2012 | Smilde et al. | |
| 2013/0265572 A1* | 10/2013 | Delgado | G01N 21/8806 356/237.5 |
| 2013/0278942 A1 | 10/2013 | Jeong et al. | |
| 2015/0338749 A1 | 11/2015 | Hinnen et al. | |

FOREIGN PATENT DOCUMENTS

| | | |
|---|---|---|
| TW | 201350830 | 12/2013 |
| WO | WO 2009/078708 | 6/2009 |
| WO | WO 2009/106279 | 9/2009 |

OTHER PUBLICATIONS

Taiwan Office Action dated Nov. 22, 2017 in corresponding Taiwan Patent Application No. 105142407.

* cited by examiner

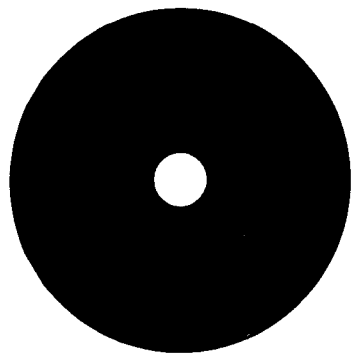
Fig. 7A
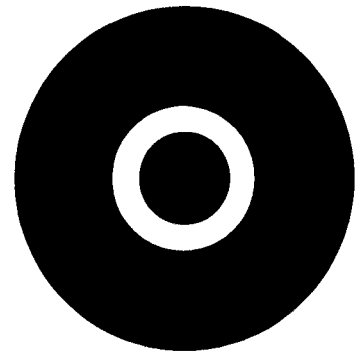
Fig. 7B
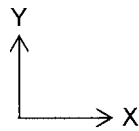
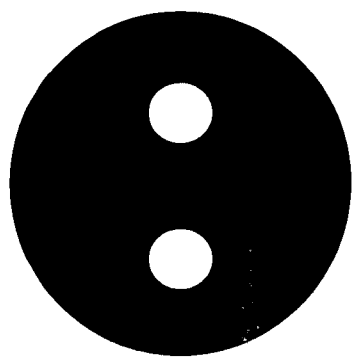
Fig. 7C
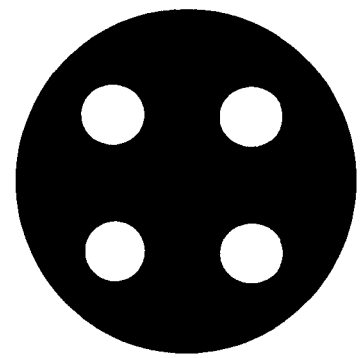
Fig. 7D

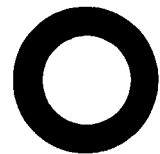
Fig. 8A                    Fig. 8B
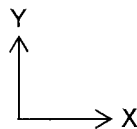
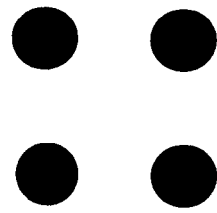
Fig. 8C                    Fig. 8D

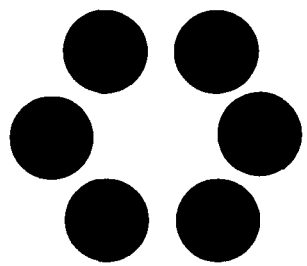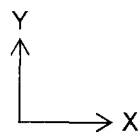
Fig. 10A          Fig. 10B

Fig. 11A
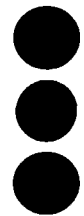
Fig. 11B
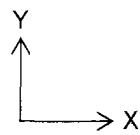
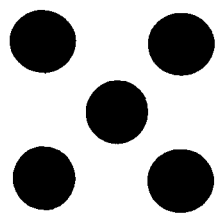
Fig. 11C
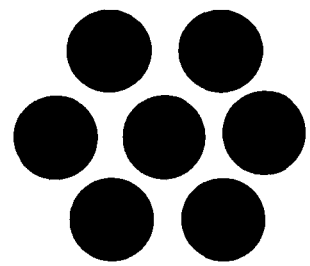
Fig. 11D

METHOD AND DEVICE FOR FOCUSING IN AN INSPECTION SYSTEM

This application claims the benefit of priority of U.S. provisional application No. 62/273,982, which was filed on Dec. 31, 2015. The content of the foregoing application is incorporated herein in its entirety by reference.

FIELD

The present description relates to a method and apparatus for inspection (e.g., metrology) usable, for example, in the manufacture of devices by a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

A lithographic apparatus can be used, for example, in the manufacture of integrated circuits (ICs) and other devices. In such a case, a patterning device (e.g., a mask) may contain or provide a pattern corresponding to an individual layer of the device ("design layout"), and this pattern can be transferred onto a target portion (e.g. comprising one or more dies) on a substrate (e.g., silicon wafer) that has been coated with a layer of radiation-sensitive material ("resist"), by methods such as irradiating the target portion through the pattern on the patterning device. In general, a single substrate contains a plurality of adjacent target portions to which the pattern is transferred successively by the lithographic apparatus, one target portion at a time. In one type of lithographic apparatuses, the pattern is transferred onto one target portion in one go; such an apparatus is commonly referred to as a wafer stepper. In an alternative apparatus, commonly referred to as a step-and-scan apparatus, a projection beam scans over the patterning device in a given reference direction (the "scanning" direction) while synchronously moving the substrate parallel or anti-parallel to this reference direction. Different portions of the pattern on the patterning device are transferred to one target portion progressively. Since, in general, the lithographic apparatus will have a magnification factor M (generally <1), the speed F at which the substrate is moved will be a factor M times that at which the beam scans the patterning device.

Prior to transferring the pattern from the patterning device to the substrate, the substrate may undergo various procedures, such as priming, resist coating and a soft bake. After exposure, the substrate may be subjected to other procedures, such as a post-exposure bake (PEB), development, a hard bake and measurement/inspection of the transferred pattern. This array of procedures is used as a basis to make an individual layer of a device, e.g., an IC. The substrate may then undergo various processes such as etching, ion-implantation (doping), metallization, oxidation, chemo-mechanical polishing, etc., all intended to finish off the individual layer of the device. If several layers are required in the device, then the whole procedure, or a variant thereof, is repeated for each layer. Eventually, a device will be present in each target portion on the substrate. These devices are then separated from one another by a technique such as dicing or sawing, whence the individual devices can be mounted on a carrier, connected to pins, etc.

As noted, lithography is a central step in the manufacturing of ICs and other devices, where patterns formed on substrates define functional elements of the devices, such as microprocessors, memory chips etc. Similar lithographic techniques are also used in the formation of flat panel displays, micro-electro mechanical systems (MEMS) and other devices.

In a lithographic process (i.e., a process of developing a device or other structure involving lithographic exposure, which may typically include one or more associated processing steps such as development of resist, etching, etc.), it is desirable frequently to make measurements of structures created, e.g., for process control and verification. Various tools for making such measurements are known, including scanning electron microscopes, which are often used to measure critical dimension (CD), and specialized tools to measure overlay, the accuracy of alignment of two layers of a substrate.

SUMMARY

In order to obtain accurate measurements (e.g., critical dimension, overlay, etc.) using an inspection apparatus (e.g., a metrology apparatus), at least the target structure on the substrate should be situated close to, or at, the focal plane of an objective of the inspection apparatus. This can be done, for example, by tuning the relative position between the focus of the objective and the target structure until the target structure on the substrate is situated close to, or at, the focal plane of the objective. Such tuning is referred to herein as focusing the substrate or target structure and may include moving the objective (and thus the focal point) relative to the target structure, changing an optical element within the objective to shift the focal point, moving the target structure relative to the focal point, or any combination selected therefrom. It is desirable to provide an improved method for focusing in an inspection apparatus.

In an embodiment, there is provided a method comprising: directing a first measurement beam of radiation onto a substrate, the first measurement beam having a first intensity distribution; and directing a second focusing beam of radiation onto the substrate at a same time as the first measurement beam is directed onto the substrate, the second focusing beam having a second intensity distribution, wherein at least part of the second intensity distribution is spatially separated from the first intensity distribution at least at the substrate and/or an aperture device.

In an embodiment, there is provided an inspection apparatus comprising: a substrate holder configured to hold a substrate; an aperture device; and an optical system configured to direct a first measurement beam of radiation onto the substrate, the first measurement beam having a first intensity distribution, and configured to direct a second focusing beam of radiation onto the substrate at a same time as the first measurement beam is directed on the substrate, the second focusing beam having a second intensity distribution, wherein at least part of the second intensity distribution is spatially separated from the first intensity distribution at least at the substrate and/or the aperture device.

Features and/or advantages of embodiments of the invention, as well as the structure and operation of various embodiments of the invention, are described in detail herein with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which.

FIGS. 7A, 7B, 7C and 7D schematically depict different types of illumination apertures;

FIGS. 8A, 8B, 8C and 8D schematically depict different illumination shapes corresponding to the illumination apertures as illustrated in FIGS. 7A-7D;

FIGS. 10A and 10B schematically depict two illumination shapes corresponding to different illumination modes using a multi-mode fiber or fiber bundle as illustrated in FIG. 9;

FIGS. 11A, 11B, 11C and 11D schematically depict different illumination shapes in a combination of both a focusing beam and a measurement beam;

DETAILED DESCRIPTION

Before describing embodiments in detail, it is instructive to present an example environment in which embodiments may be implemented.

Figure 1:
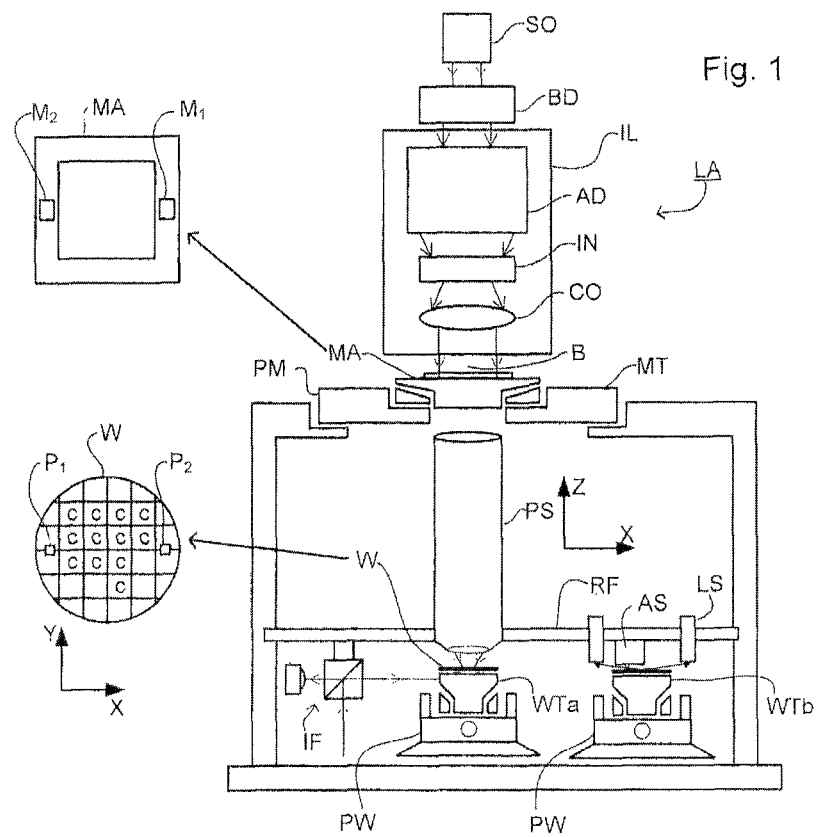
FIG. 1 schematically depicts a lithographic apparatus according to an embodiment.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate.

An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular and/or spatial intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. An embodiment of an alignment system, which can detect the alignment markers, is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two tables WTa, WTb (e.g., two substrate tables) and two stations—an exposure station and a measurement station—between which the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

Figure 2:
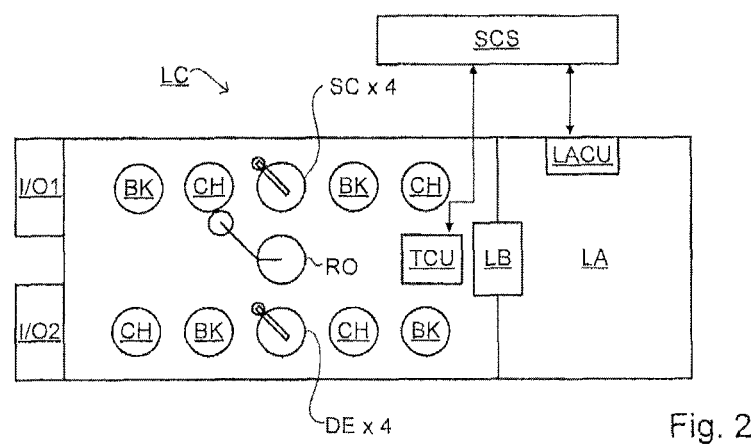
FIG. 2 schematically depicts a lithographic cell or cluster according to an embodiment.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

A target used by a conventional scatterometer comprises a relatively large periodic structure layout (e.g., comprising one or more gratings), e.g., 40 μm by 40 μm. In that case, the measurement beam often has a spot size that is smaller than the periodic structure layout (i.e., the layout is underfilled such that one or more of the periodic structures is not completely covered by the spot). This simplifies mathematical reconstruction of the target as it can be regarded as infinite. However, for example, so the target can be positioned in among product features, rather than in the scribe lane, the size of a target has been reduced, e.g., to 20 μm by 20 μm or less, or to 10 μm by 10 μm or less. In this situation, the periodic structure layout may be made smaller than the measurement spot (i.e., the periodic structure layout is overfilled). Typically such a target is measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay using dark-field detection of the diffraction orders enables overlay measurements on smaller targets. These targets can be smaller than the illumination spot and may be surrounded by product structures on a substrate. In an embodiment, multiple targets can be measured in one image.

In an embodiment, the target on a substrate may comprise one or more 1-D periodic gratings, which are printed such that after development, the bars are formed of solid resist lines. In an embodiment, the target may comprise one or more 2-D periodic gratings, which are printed such that after development, the one or more gratings are formed of solid resist pillars or vias in the resist. The bars, pillars or vias may alternatively be etched into the substrate. The pattern of the grating is sensitive to chromatic aberrations in the lithographic projection apparatus, particularly the projection system PL, and illumination symmetry and the presence of such aberrations will manifest themselves in a variation in the printed grating. Accordingly, the measured data of the printed gratings can be used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other measurement processes.

Figure 3A:
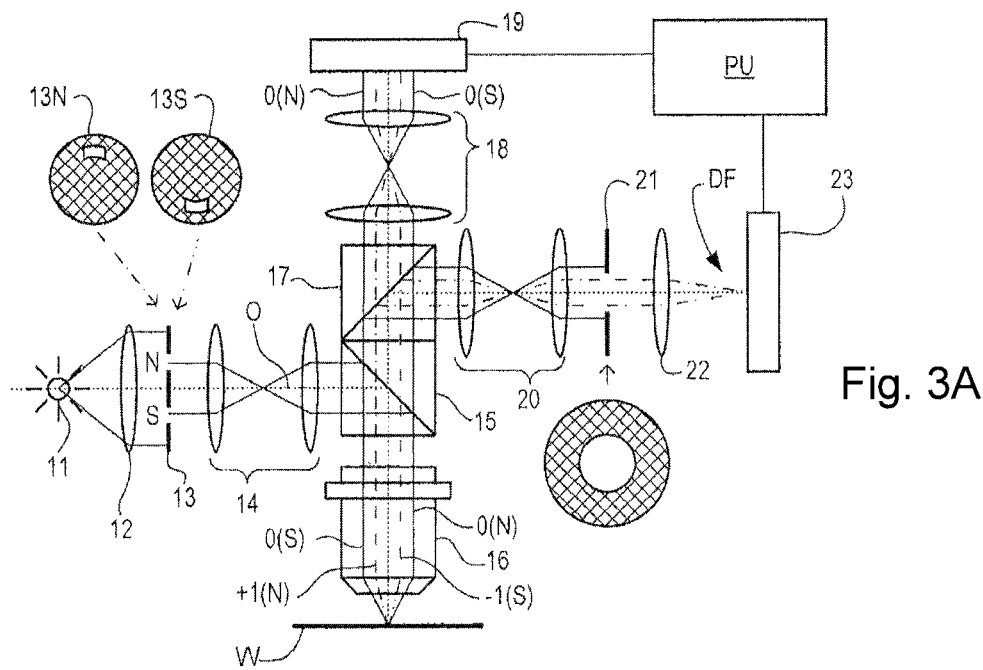
FIG. 3A is schematic diagram of a dark field measurement apparatus for use in measuring targets according to an embodiment using a first pair of illumination apertures providing certain illumination modes.

A dark field metrology apparatus suitable for use in embodiments is shown in FIG. 3A. A target T (comprising a periodic structure such as a grating) and diffracted rays are illustrated in more detail in FIG. 3B. The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture device 13 of suitable form between lenses 12 and 14, in a plane which is a back-projected image of the objective pupil plane. In the example illustrated, aperture device 13 has different forms, labeled 13N and 13S, allowing different illumination modes to be selected. The illumination system in the present examples forms an off-axis illumination mode. In the first illumination mode, aperture device 13N provides off-axis illumination from a direction designated, for the sake of description only, as 'north'. In a second illumination mode, aperture device 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

Figures 3B, 3C, 3D:
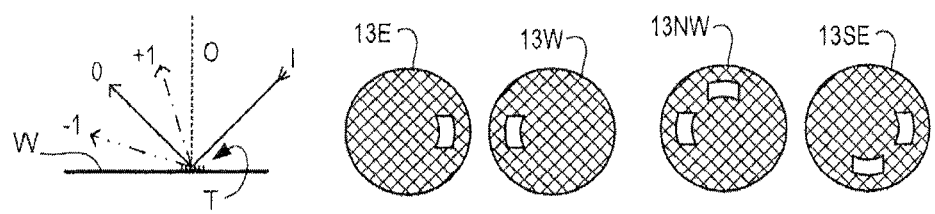
FIG. 3B is a schematic detail of a diffraction spectrum of a target for a given direction of illumination.
FIG. 3C is a schematic illustration of a second pair of illumination apertures providing further illumination modes in using a measurement apparatus for diffraction based overlay measurements.
FIG. 3D is a schematic illustration of a third pair of illumination apertures combining the first and second pairs of apertures providing further illumination modes in using a measurement apparatus for diffraction based overlay measurements.

As shown in FIG. 3B, target T is placed with substrate W substantially normal to the optical axis O of objective 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Since the aperture in device 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective are closely aligned with the central optical axis. The rays illustrated in FIGS. 3A and 3B are shown somewhat off axis, purely to enable them to be more easily distinguished in the diagram.

At least the 0 and +1 orders diffracted by the target on substrate W are collected by objective 16 and directed back through prism 15. Returning to FIG. 3A, both the first and second illumination modes are illustrated, by designating diametrically opposite apertures labeled as north (N) and south (S). When the incident ray I is from the north side of the optical axis, that is when the first illumination mode is applied using aperture device 13N, the +1 diffracted rays, which are labeled +1(N), enter the objective 16. In contrast, when the second illumination mode is applied using aperture device 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the −$1^{st}$ and the +$1^{st}$ diffraction order intensities. Comparing these intensities for a given target provides a measurement of asymmetry in the target, and asymmetry in the target can be used as an indicator of a parameter of a lithography process, e.g., overlay error. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not described in detail here.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image DF of the target formed on sensor 23 is formed from the −1 or +1 first order beam. The images captured by sensors 19 and 23 are output to processor and controller PU, the function of which will depend on the particular type of measurements being performed. Note that the term 'image' is used here in a broad sense. An image of the periodic structure features (e.g., grating lines) as such will not be formed, if only one of the −1 and +1 orders is present.

The particular forms of aperture device 13 and stop 21 shown in FIG. 3 are purely examples. In another embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture device 13 may comprise a number of aperture patterns formed around a disc, which rotates to bring a desired pattern into place. Note that aperture device 13N or 13S are used to measure a periodic structure of a target oriented in one direction (X or Y depending on the set-up). For measurement of an orthogonal periodic structure, rotation of the target through 90° and 270° might be implemented. Different aperture devices are shown in FIGS. 3C and D. FIG. 3C illustrates two further types of off-axis illumination mode. In a first illumination mode of FIG. 3C, aperture device 13E provides off-axis illumination from a direction designated, for the sake of description only, as 'east' relative to the 'north' previously described. In a second illumination mode of FIG. 3C, aperture device 13W is used to provide similar illumination, but from an opposite direction, labeled 'west'. FIG. 3D illustrates two further types of off-axis illumination mode. In a first illumination mode of FIG. 3D, aperture device 13NW provides off-axis illumination from the directions designated 'north' and 'west' as previously described. In a second illumination mode, aperture device 13SE is used to provide similar illumination, but from an opposite direction, labeled 'south' and 'east' as previously described. The use of these, and numerous other variations and applications of the apparatus are described in, for example, the prior published patent application publications mentioned above.

Figure 4A:
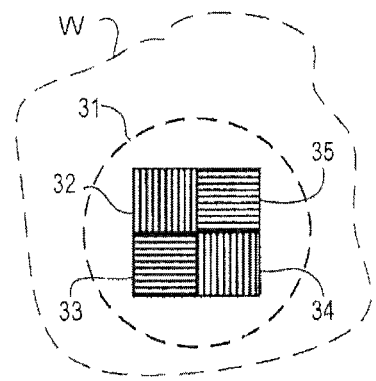
FIG. 4A schematically depicts a form of multiple periodic structure (e.g., multiple grating) target and an outline of a measurement spot on a substrate.

FIG. 4A depicts an example composite metrology target formed on a substrate. The composite target comprises four periodic structures (in this case, gratings) 32, 33, 34, 35 positioned closely together. In an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e.g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs.

Returning to FIG. 4A, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in the image captured by sensor 23.

Figure 4B:
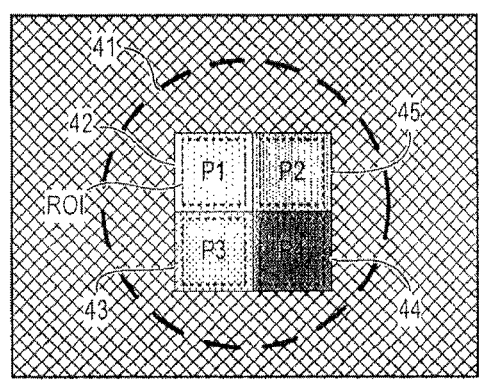
FIG. 4B schematically depicts an image of the target of FIG. 4A obtained in the apparatus of FIG. 3.

FIG. 4B shows an example of an image that may be formed on and detected by the sensor 23, using the target of FIG. 4A in the apparatus of FIG. 3, using the aperture devices 13NW or 13SE from FIG. 3D. While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. If the periodic structures are located in product areas, product features may also be visible in the periphery of this image field. Processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

The measurement accuracy and/or sensitivity of the target may vary with respect to one or more characteristics of the beam of radiation provided onto the target, for example, the wavelength of the radiation beam, the polarization of the radiation beam, and/or the intensity distribution (i.e., angular or spatial intensity distribution) of the radiation beam. In an embodiment, the wavelength range of the radiation beam is limited to one or more wavelengths selected from a range (e.g., selected from the range of about 400 nm to 900 nm). Further, a selection of different polarizations of the radiation beam may be provided and various illumination shapes can be provided using, for example, a plurality of different apertures.

Further, to obtain accurate measurements (e.g., CD, overlay, etc. measurements), at least the target structure on the substrate should be situated at, or near, the focal plane of an objective of the inspection apparatus (e.g., a metrology apparatus). As discussed above, this can be done by focusing the target structure, whether by changing the focus point of the optical system and/or by providing relative movement between the substrate and the focus point (e.g., by moving the substrate, at least part of the optical system, or both).

Figure 5A:
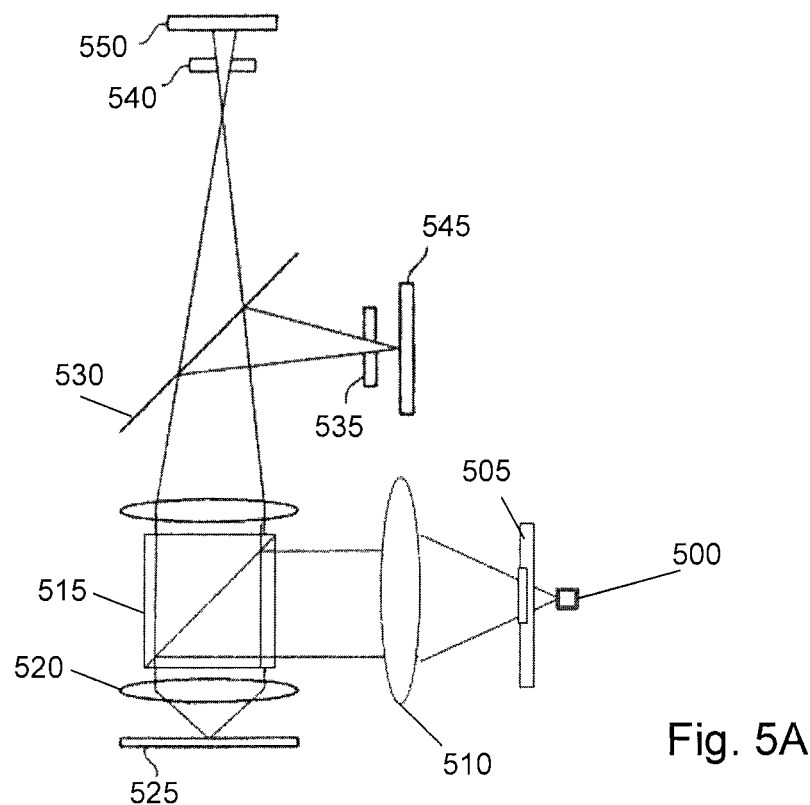
FIG. 5A schematically depicts an embodiment of a confocal focus sensor system that can be used in an inspection apparatus.

In an embodiment, to provide focus control, a focus sensor system with a confocal optical system can be used in an inspection apparatus (e.g., in an overlay and/or CD measurement apparatus) and/or lithographic apparatus. The focus sensor system can generate a focus error signal which can be used as part of a control loop to ensure that the substrate is in focus. An example layout of focus sensor system with a confocal optical system is depicted in FIG. 5A. In the system, radiation is provided by an input 500 (e.g., a radiation source) to an illumination field stop 505. From the stop 505, the radiation passes via a condenser lens 510 to an optical element (e.g., a beam splitter) 515, which directs the beam to an objective 520. The radiation is output from objective 520 to substrate 525. The radiation redirected by the substrate 525 passes via objective 520 and optionally optical element 515 to a beam splitter 530 in the detection branch. A portion of the beam is provided to aperture 535 and another portion is provided to aperture 540. In an embodiment, apertures 535, 540 are pinhole apertures provided, e.g., in respective plates. In an embodiment, one of the apertures 535, 540 is a different distance from the beam splitting surface of the beam splitter 530 than the other aperture 535, 540. Associated with each of the apertures 535, 540 is a respective detector 545, 550 to receive the respective portion of radiation from the respective apertures 535, 540. In an embodiment, the detectors are photo-detectors.

Figure 5B:
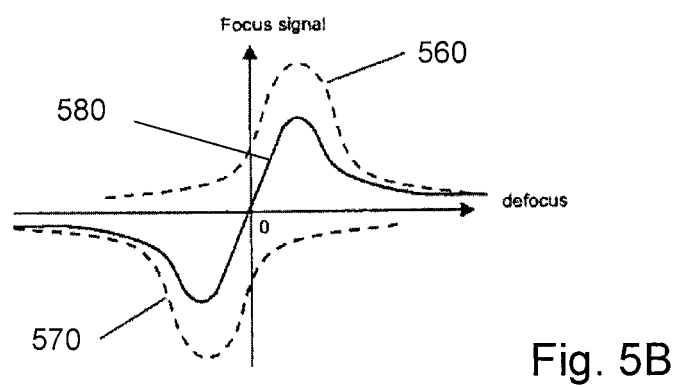
FIG. 5B schematically illustrates focus error signals that can be generated from the sensor system of FIG. 5A.

In an embodiment, the system of FIG. 5A generates a focus error signal for the substrate using a signal 560 from, e.g., the combination of aperture 535 and detector 545, and a signal 570 from, e.g., the combination of aperture 540 and detector 550. In an embodiment, signal 570 is subtracted from signal 560 to produce focus error signal 580 for the substrate as shown in FIG. 5B.

A problem with this arrangement in an inspection apparatus can be that the focus spot (which is for keeping the substrate in focus of the inspection apparatus) can overlap with a measurement spot provided by the inspecting branch of the inspection apparatus (which spot is not shown in FIG. 5) that is used for inspecting or measuring the substrate. This overlap may prevent simultaneous operation of the focusing and inspecting operations/branches. In an embodiment, simultaneous use can be obtained by using spectral separation and interference filters, but this can cause one or more additional limitations, such as the wavelength ranges that can be used for inspection.

Thus, in an embodiment, there is provided an improved focusing apparatus and/or method for an inspection apparatus to, for example, enable improved accuracy and/or sensitivity in measurements and/or enable improved spectral range of operation for an inspection apparatus (e.g., overlay and/or CD measurement apparatus).

Figure 6:
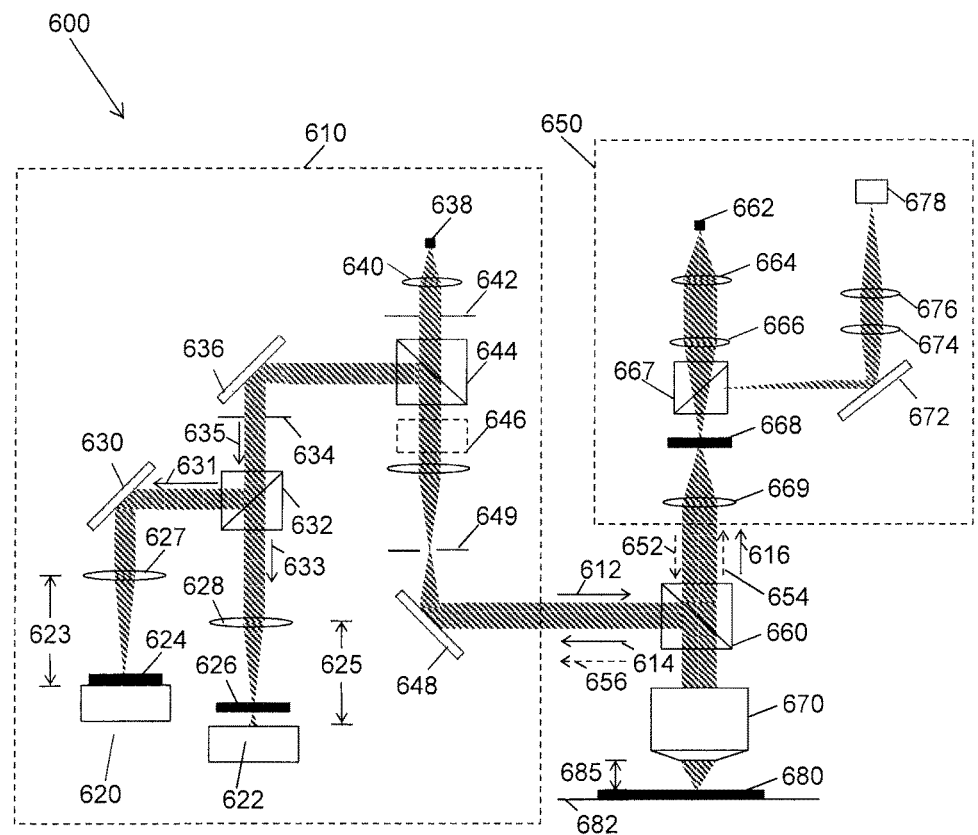
FIG. 6 schematically depicts an inspection apparatus according to an embodiment.

FIG. 6 depicts a schematic illustration of an example inspection apparatus 600 (e.g., metrology apparatus) configured to provide focusing and provide optical measurement of, for example, CD, overlay, etc. As shown in FIG. 6, the inspection apparatus 600 comprises a focusing module 610, a measurement module 650, a partially reflective optical element 660, an objective 670, and a substrate holder 682 configured to hold a substrate 680.

The focusing module 610, the partially reflective optical element 660, and the objective 670 are collectively configured to determine whether a target, e.g., on the substrate 680 and/or the substrate 680 itself, is situated at or near a focal plane of the objective 670, and how to provide relative spatial adjustment between the focal point and the target, e.g., relative spatial adjustment between the focal point and the target (e.g., through movement of the objective 670, and/or through movement of the substrate, etc.). For example, in an embodiment, the relative spatial adjustment makes the working distance 685 equal to, or close to, the focal length of the objective 670 when the target on the substrate 680 is determined to be not situated at or near the focal plane of the objective 670.

Specifically, to enable determining whether the target is at or near the focal point, a focusing beam 612 emitted by a first input 638 (e.g., a radiation source such as a lamp or laser, or an input to the focusing module 610 connected or connectable to a radiation source) is directed toward the partially reflective optical element 660 from the focusing module 610 by an optical system comprising a lens 640, an aperture stop 642, a partially reflective optical element 644, and a reflective optical element 648 in the illumination path of the focusing module. The first input 638 is situated at or near the focal plane of the lens 640 so that radiation emitted by the first input 638 can be converted to a collimated beam of radiation as shown in FIG. 6. The aperture stop 642 is configured to control the amount of the collimated beam of radiation transmitted toward the partially reflective optical element 644, for example, by adjusting the aperture width of the aperture stop 642. The focusing beam 612 is further directed toward the target on the substrate 680 by the reflective optical element 648, the partially reflective optical element 660 and the objective 670, and subsequently redirected (e.g., diffracted, reflected, etc.) by the target on, for example, the substrate 680.

The redirected focusing beam is collected by the objective 670 and directed back toward the focusing module 610 by, e.g., partially reflective optical element 660. Specifically, at least a portion of the redirected focusing beam 614 (i.e., the beam 635) is directed to a beam splitter 632 by the objective 670, the partially reflective optical element 660, the reflective optical element 648, the partially reflective optical element 644, the reflective optical element 636, and the aperture stop 634 (which is similar to the aperture stop 642), successively in the detection path of the focusing module. The beam splitter 632 divides the beam 635 into a first focusing beam part 631 and a second focusing beam part 633 with desirably substantially equal intensities. The beam splitter 632 further directs the first focusing beam part 631 to a first detection branch, and directs the second focusing beam part 633 to a second detection branch.

In the first detection branch, the first focusing beam part 631 is further directed to a first detector 620 through the use of a first optical system comprising a reflective optical element 630, a lens 627, and a first aperture device 624 placed after the image plane of lens 627 along the beam direction. The first detector 620 is configured to characterize, for example, the intensity of the detected beam of radiation by the first detector 620. The measurement of the detected beam of radiation by the first detector 620 may be further output to a processor (not shown).

In the second detection branch, the second focusing beam part 633 is directed to a second detector 622 through the use of a second optical system comprising a lens 628 and a second aperture device 626 placed before the image plane of lens 628 along the beam direction. The second detector 622 is configured to characterize, for example, the intensity of the detected beam of radiation by the second detector 622. The measurement of the detected beam of radiation by the second detector 622 may be further output to a processor (not shown).

In an embodiment, the focusing module 610 uses intensity difference to determine the relative position between the focal point of objective 670 and the target and will be described further herein. However, focusing module 610 may use a different technique to derive the relative position between the focal point and the target, such as phase difference, etc.

In an embodiment, the lens 627 and the first aperture device 624 are substantially similar to the lens 628 and the second aperture device 626, respectively.

The aperture shapes of the first aperture device 624 and the second aperture device 626 can be similar to the aperture shape of the beam of radiation generated by, for example, the first input 638, or of arbitrary shape. However, the aperture sizes of the first aperture device 624 and the second aperture device 626 are appropriately selected and positioned (and calibrated by measuring intensities when, e.g., the target is at the focal plane) to enable focus position determination by, for example, differentiating responses from detectors 620 and 622. This is designed so that it can be determined whether the target is approximately situated on the focal plane of the objective 670 by comparing the intensities of the beams detected by the first detector 620 and second detector 622. For example, equal intensities measured at both detectors may signify that the target is at or near the focal plane of the objective 670. Unequal intensity between detectors 620 and 622 indicates an out of focus condition, where the direction and amount of focus offset is determined by the difference in signal. Specific defocus values can be determined by calibration.

As a result of the determination made using the information from the first detector 620 and the second detector 622, the processor may instruct one or more actuators to provide focusing by, e.g., shifting the position of the objective 670 in the Z direction, the substrate holder 682 in the Z direction, or both. This focusing may be by a specific amount determined by the processor (e.g., a specific value obtained through calibrations). Additionally or alternatively, the intensity of the beam of radiation detected by the first detector 620 and the second detector 622 may be monitored to identify whether the target substantially coincides with the focal point of the objective 670.

The measurement module 650, the partially reflective optical element 660, and the objective 670 are collectively configured to measure the target of the substrate 680 to determine, for example, CD, overlay, focus, dose, etc. Specifically, a measurement beam 652 emitted by a second input 662 (e.g., a radiation source such as a lamp or laser, or an input connected or connectable to a radiation source) is directed toward the partially reflective optical element 660 from the measurement module 650 by an optical system comprising lenses 664, 666, a partially reflective optical element 667 and lens 669. The measurement beam 652 is further directed onto the target by the partially reflective optical element 660 and the objective 670, and subsequently radiation from the measurement beam 652 is redirected by the target. At least a portion of the redirected measurement beam 654 is collected by the objective 670 and directed toward the detector 678 (e.g. a CCD or CMOS sensor) via the objective 670, the partially reflective optical element 660, the lens 669, the partially reflective optical element 667, a reflective optical element 672, a lens 674 and a lens 676. The lenses 674 and 676 are arranged in a double sequence of a 4F arrangement. A different lens arrangement can be used, provided that it still provides the radiation of the target onto the detector 678.

As shown in FIG. 6, the focusing module 610 and the measurement module 650 may operate simultaneously. That is, at a point in time, both the focusing beam 612 and the measurement beam 652 are incident on the substrate 680. Advantageously, the relative position between the focal point of the objective 670 and the target on the substrate 680 may be automatically adjusted in real-time whenever the substrate 680 is not within a specific range of the focal plane of the objective 670.

However, in addition to the portion of the redirected focusing beam 614, a portion of the redirected measurement beam 656 may be divided from the redirected measurement beam by the partially reflective optical element 660 and be further directed to the focusing module for detection in the first detector 620 and the second detector 622. The leakage of a portion of the redirected measurement beam to the first detector 620 and/or the second detector 622 adversely affects the accuracy and/or sensitivity of focusing. Additionally or alternatively, a portion of the redirected focusing beam 616 may be divided from the redirected focusing beam by the partially reflective optical element 660 and be further directed to the measurement module for detection in the detector 678. Accordingly, the leakage of the redirected focusing beam to the detector 678 adversely affects the accuracy and/or sensitivity of measurement.

A solution to this problem is implemented by spectrally separating the redirected focusing beam and the redirected measurement beam. This may be done by employing focusing and measurement beams with different wavelengths and/or non-overlapping spectral bandwidths. Accordingly, one or more notch filters corresponding to the wavelength and/or bandwidth of the measurement beam may be inserted in the focusing module 610 (e.g., between the partially reflective optical element 644 and the reflective optical element 636) to block the portion of the redirected measurement beam 656. Similarly, one or more notch filters corresponding to the wavelength and/or bandwidth of the focusing beam may be inserted in the measurement module 650 (e.g., between the partially reflective optical element 667 and the reflective optical element 672) to block the portion of the redirected focusing beam 616.

However, since the wavelengths and/or bandwidths of the measurement and focusing beams are non-overlapping, the choices of the wavelengths and/or bandwidths of the focusing and measurement beams are limited. Further, if different combinations of measurement and focusing beam are desired, there will be a delay in switching the filter (e.g., a time for switching the wavelength and/or bandwidth of a notch filter can be as slow as 500 milliseconds), which thereby limits the throughput. And, notch filters can be difficult and/or expensive to fabricate. Therefore, it is desired to provide an effective approach of separating the redirected focusing and measurement beams.

According to an embodiment of the disclosure, the redirected focusing beam and the redirected measurement beam may be spatially separated by providing the focusing beam 612 and the measurement beam 652 with suitable illumination shapes such that the focusing beam 612 and the measurement beam 652 do not overlap, or overlap less than the majority of each beam spot. Additionally or alternatively, by, e.g., providing appropriate aperture shapes for the aperture devices 624 and 626, the portion of the redirected measurement beam 656 may be prevented from reaching the detectors 620 and 622 in the focusing module 610. Similarly, additionally or alternatively, the portion of the redirected focusing beam 616 may be prevented from reaching the detector 678 in the measurement module 650 by providing, e.g., an appropriate aperture shape for an aperture device 668 (as shown in FIG. 6).

In an embodiment, the focusing beam is provided with an intensity distribution such that the radiation is off-axis (e.g., annular, dipole, quadrupole, etc.), while the measurement beam is provided with an intensity distribution that is on-axis (e.g., circular) such that all, or a majority, of the focusing beam is spatially outward of the measurement beam radiation at least at the target/substrate and/or an aperture device. In an embodiment, the measurement beam is provided with an intensity distribution such that the radiation is off-axis (e.g., annular, dipole, quadrupole, etc.), while the focusing beam is provided with an intensity distribution that is on-axis (e.g., circular) such that all, or a majority, of the measurement beam is spatially outward of the focusing beam radiation at least at the target/substrate and/or an aperture device.

Referring back to FIG. 6, in an embodiment, the first input 638 and/or the second input 662 may provide the radiation with the desired intensity distribution. Additionally or alternatively, a beam shaping optical element (e.g., a diffractive optical element, an axicon (pair), a spatial light modulator, a wedge pyramid, etc.) can be provided in the path of the measurement beam and/or the focusing beam to redirect the radiation to provide the desired intensity distribution. Additionally or alternatively, an aperture device (e.g., a plate with an opening, a spatial light modulator to effectively provide an opening by blocking/reflecting unwanted radiation out of the optical path, a liquid crystal element to block/reflect unwanted radiation out of the optical path, etc.) may be provided in the path of the measurement beam and/or the focusing beam to provide an aperture that defines a desired spatial intensity distribution. Similarly, in an embodiment, a beam shaping optical element and/or an aperture device can be provided to prevent the portion of the redirected measurement beam 656 from reaching the detectors 620, 622 in the focusing module 610. Similarly, additionally or alternatively, the portion of the redirected focusing beam 616 may be prevented from reaching the detector 678 in the measurement module 650 using a beam shaping optical element and/or an aperture device. Further, it will be appreciated different combinations of the devices may be used to arrive at the desired intensity distribution and/or prevent radiation from reaching detectors. For example, a beam shaping optical element may provide the desired intensity distribution while an aperture device may prevent radiation from reaching the detectors.

As mentioned above, in an embodiment, an aperture device is provided to create a desired intensity distribution (also referred to as illumination shape). The aperture device for the focusing beam may be the input 638 (e.g., a fiber), an aperture device provided in a field plane (e.g., at input 638) or aperture device 642 (e.g., in the form of an angular shaping device). The aperture device for the measurement beam may be aperture device 668. The aperture device may be a plate with one or more openings defining the illumination shape(s). For example, the aperture plate may comprise a plurality of openings, each opening defining a different illumination shape and the plate being movable (e.g., rotatable) so that the different openings can be placed in the applicable beam path. In an embodiment, a plurality of aperture plates may be provided and placed into and out of the path of the applicable radiation. Other forms of the aperture device may include a spatial light modulator to effectively provide an illumination opening by blocking/reflecting unwanted radiation out of the optical path, a liquid crystal element to block/reflect unwanted radiation out of the optical path, etc. Various embodiments of the illumination openings of an aperture device are illustrated in FIGS. 7A-7D, including a monopole illumination opening as shown in FIG. 7A, an annular ring illumination opening as shown in FIG. 7B, a dipole illumination opening as shown in FIG. 7C, and a quadrupole illumination opening as shown in FIG. 7D. The corresponding illumination shapes of the radiation beam created by the illumination openings in FIGS. 7A-7D are illustrated in FIGS. 8A-8D (where, for convenience and to distinguish from FIG. 7, the illumination is illustrated as being dark on a white background while in practice the optical path would likely be dark with bright illumination). The monopole illumination shape as shown in FIG. 8A is sometimes referred to as on-axis illumination. The other three illumination shapes as shown in FIGS. 8B-8D are sometimes referred to as off-axis illumination. Although only four examples of the illumination openings are shown in FIGS. 7A-7D, other suitable illumination openings may be provided.

In an embodiment, a beam shaping element is provided in the optical path of the focusing beam and/or the measurement beam. In an embodiment, the beam shaping element is effectively configured to convert radiation from one intensity distribution to a different desired intensity distribution such as, for example, convert an on-axis illumination shape to an off-axis illumination shape (or vice versa) (e.g., for creating a desired illumination shape for the focusing and/or measurement beam) or to reverse the shape of radiation such that off-axis radiation is put on-axis and on-axis radiation is put off-axis (or vice versa) (e.g., for preventing radiation from reaching a detector when used in combination with, e.g., an aperture device). In an embodiment, the beam shaping element is positioned in the optical path so that it further can convert any off-axis radiation to on-axis radiation and convert any on-axis radiation to off-axis radiation (or vice versa) when radiation passes the beam shaping element in the reverse direction. Where the beam shaping element does not provide conversion of the illumination intensity distribution in the reverse direction, the beam shaping element would typically be located between input 662 and element 667 for the measurement beam and/or between input 638 and element 644 for the focusing beam. Where the beam shaping element provides conversion of the radiation intensity distribution in the reverse direction, the beam shaping element would typically be located in the optical path between detector 678 and the element 660 for the measurement beam and/or in the optical path between aperture devices 624, 626 and the element 660 (such as beam shaping element 646) for the focusing beam. In an embodiment, the beam shaping element is located at or near a pupil plane, or an optically conjugate plane thereof.

A beam shaping element may be, e.g., in the form of a diffractive optical element, an axicon, a spatial light modulator, etc. In an embodiment, the beam shaping element comprises an axicon lens configured to convert an on-axis radiation shape to a ring shape (e.g., FIG. 8B) in a first direction. Optionally, the axicon lens may be positioned so as to convert a ring shape to an on-axis illumination shape in the reverse direction.

In an embodiment, the beam shaping element comprises a pair of axicon lenses configured to convert an on-axis illumination shape to a ring shape (e.g., FIG. 8B) with adjustable radius in a first direction. By tuning the distance between the pair of axicon lenses, the radius of the ring can be changed. Optionally, the pair of axicon lenses may be positioned so as to convert a ring shape to an on-axis illumination shape in the reverse direction.

In an embodiment, the beam shaping element comprises one or more prisms (e.g., a pyramidal prism, two or more wedges) configured to convert an on-axis illumination shape to a multi-spot shape (e.g., a four spot shape as illustrated in FIG. 8D for a pyramidal prism or four wedges, a two spot shape as illustrated in FIG. 8C for two edges) in a first direction. Optionally, the one or more prisms may be positioned so as to convert a multi-spot shape to an on-axis illumination shape in the reverse direction.

Figure 9:
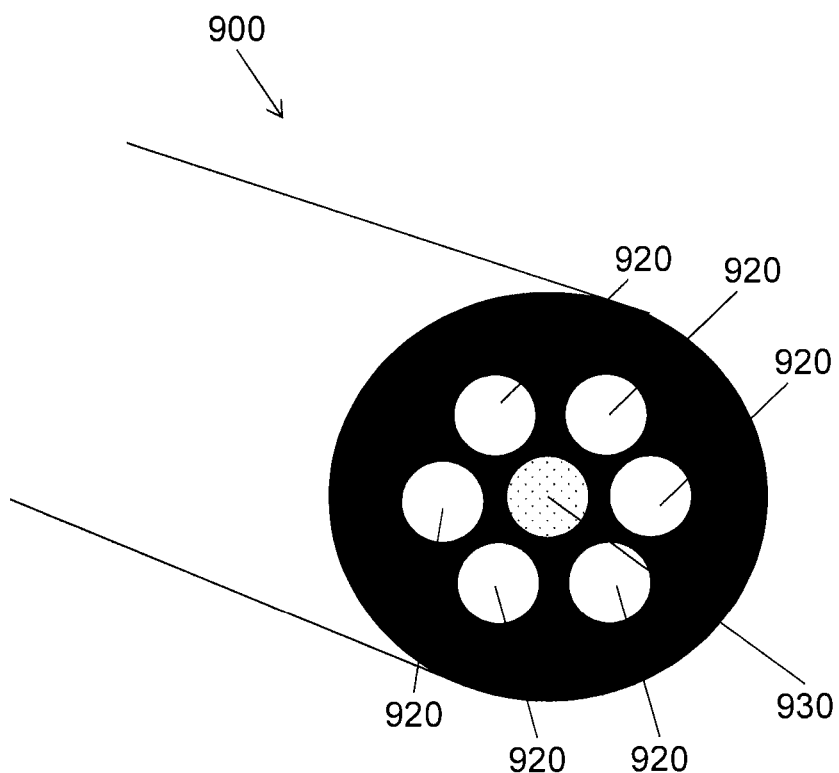
FIG. 9 schematically depicts a cross-section of a multi-core fiber or a fiber bundle.

In an embodiment, the first input 638 and/or the second input 662 comprises a multicore fiber 900 as illustrated in FIG. 9. The multicore fiber 900 comprises one or more cores 930 in the center and, in this example, 6 cores 920 around the central core 930 forming a hexagonal shape. In a first illumination mode, only the central core 930 emits radiation as shown in FIG. 10A (where, for convenience and to distinguish from FIG. 9, the illumination is illustrated as being dark on a white background while in practice the optical path would likely be dark with bright illumination), providing on-axis illumination. In a second illumination mode, one or more of the surrounding cores 920 emits radiation as shown in FIG. 10B (where, for convenience and to distinguish from FIG. 7, the illumination is illustrated as being dark on a white background while in practice the optical path would likely be dark with bright illumination), providing off-axis illumination. Although six cores 920 around the central core 930 are illustrated in FIG. 9, any suitable number of cores 920 may be provided around the central core 930. Further, although a single core 930 is illustrated in FIG. 9, any suitable number of cores 930 may be provided.

In an embodiment, the first input 638 and/or the second input 662 comprises a fiber bundle 900 as illustrated in FIG. 9. The fiber bundle 900 comprises one or more fibers situated in the center 930 and, in this example, 6 fibers 920 situated around the central fiber 930 forming a hexagonal shape. In a first illumination mode, only the central fiber 930 emits radiation as shown in FIG. 10A, providing on-axis illumination. In a second illumination mode, one or more of the surrounding cores 920 emits radiation as shown in FIG. 10B, providing off-axis illumination. Although only six fibers 920 around the central fiber 930 are illustrated in FIG. 9A, any suitable number of fibers 920 may be provided around the central fiber 930. Further, although a single fiber 930 is illustrated in FIG. 9, any suitable number of fibers 930 may be provided.

In an embodiment, where the first input 638 comprises a multicore fiber or a fiber bundle, all the cores or fibers may emit radiation at once. In a variant, where the focusing beam 612 fully overlaps the measurement 652 at the substrate 680, at least one or more inner cores or fibers emit radiation when the measurement beam 652 has an on-axis shape such the focusing beam 612 fully overlaps the measurement 652 at the substrate 680. Similarly, at least one or more outer cores or fibers emit radiation when the measurement beam 652 has an off-axis shape such that the focusing beam 612 fully overlaps the measurement 652 at the substrate 680.

Referring back to FIG. 6, in an embodiment, the focusing beam 612 has an off-axis illumination shape (e.g., as shown in FIGS. 8B-8D or FIG. 10B) by, for example, using an aperture device near an intermediate image plane (e.g., an aperture device having the opening as illustrated in FIG. 7B, 7C, or 7D, and located, e.g., at the position of 646), operating in the second illumination mode using the multi-core fiber or the fiber bundle 900 as discussed above or using a beam shaping element (such as beam shaping device 646). Therefore, the focusing beam 612 may have an illumination shape similar to one of the illumination shape as shown in FIGS. 8B-8D or FIG. 10B. Accordingly, the measurement beam 652 has on-axis illumination shape (e.g., as shown in FIG. 8A or FIG. 10A) by, for example, using an aperture device (e.g., an aperture device having the opening as illustrated in FIG. 7A, and being, e.g., aperture device 668), operating in the first illumination mode using the multicore fiber or the fiber bundle 900, or using a beam shaping element (e.g., located between lens 669 and aperture device 668). As a result, the focusing beam 612 and the measurement beam 652 may collectively form a spatially separated illumination shape, for example, as shown in one of the illumination shapes in FIG. 11A-11D (where, for convenience and to distinguish from FIG. 10, the illumination is illustrated as being dark on a white background while in practice the optical path would likely be dark with bright illumination).

Similarly, in this embodiment, the portion of the redirected focusing beam 614 and the portion of the redirected measurement beam 656 may collectively form a spatially separated illumination shape, for example, as shown in one of the illumination shapes in FIG. 11A-11D. In addition, both the portion of redirected focusing beam 614 and the portion of the redirected measurement beam 656 are directed to the focusing module 610. By using an appropriate first aperture device 624 and second aperture device 626 whose aperture opening shape blocks or reflects the portion of the redirected measurement beam 656 (e.g., an opening having the shape of, e.g., FIG. 7B-7D), the portion of the redirected measurement beam 656 is prevented from reaching the detectors 620, 622 in the focusing module 610. The aperture devices 624, 626 may be used with a beam shaping element as discussed further hereafter.

Further, the portion of the redirected focusing beam 616 and the portion of the redirected measurement beam 654 may collectively form the same spatially separated illumination shape. In addition, both the portion of the redirected focusing beam 616 and the portion of the redirected measurement beam 654 are directed to the measurement module 650. By using an appropriate aperture device 668 whose aperture opening shape blocks or reflects the portion of the redirected focusing beam 616 (e.g., an opening having the shape of, e.g., FIG. 7A), the portion of the redirected focusing beam 616 is prevented from reaching the detector 678 in the measurement module 650. For example, the aperture device 668 may be a pinhole with appropriate size so that the portion of the redirected focusing beam 616 is blocked completely while the portion of the redirected measurement beam 654 is not blocked. The aperture device 668 may be used with a beam shaping element as discussed further hereafter. As shown in FIG. 6, the aperture device 668 is provided at or near the focal planes of the lenses 666 and 669. However, the aperture device 668 instead may be provided in any suitable location between the partially reflective optical element 667 and the detector 678 in the path of radiation from the substrate 680 toward the detector 678. In an embodiment, the aperture device 668 is located at or near an intermediate image plane, or an optically conjugate plane thereof.

Referring back to FIG. 6, in an embodiment, the focusing beam 612 has on-axis illumination shape (e.g., as shown in FIG. 8A or FIG. 10A) by, for example, using an aperture device (e.g., an aperture device having the opening as illustrated in FIG. 7A, and located, e.g., between input 638 and element 660 at, e.g., the position of 646, with an additional relay between 640 and 660), operating in the first illumination mode using the multicore fiber or the fiber bundle 900 as discussed above, or using a beam shaping element (e.g., beam shaping element 642 at a pupil plane or optically conjugate plane). Similarly, the measurement beam 652 has an off-axis illumination shape (e.g., as shown in FIGS. 8B-8D or FIG. 10B) by, for example, using an aperture device (e.g., aperture device 668 having the opening as illustrated in FIG. 7B, 7C, or 7D), operating in the second illumination mode using the multicore fiber 900 or the fiber bundle 900, or using a beam shaping element (e.g., located between lens 669 and input 662). As a result, the focusing beam 612 and the measurement beam 652 may collectively form a spatially separated illumination shape, for example, as shown in one of the illumination shapes in FIG. 11A-11D.

Similarly, in this embodiment, the portion of the redirected focusing beam 614 and the portion of the redirected measurement beam 656 may collectively form a spatially separated illumination shape, for example, as shown in one of the illumination shapes in FIG. 11A-11D. In addition, the portion of redirected focusing beam 614 and the portion of the redirected measurement beam 656 are directed to the focusing module 610. By using an appropriate first aperture device 624 and second aperture device 626 whose aperture opening shape blocks or reflects the portion of the redirected measurement beam 656 (e.g., an opening having the shape of, e.g., FIG. 7A), the portion of the redirected measurement beam 656 is prevented from reaching the detectors 620, 622 in the focusing module 610. The aperture devices 624, 626 may be used with a beam shaping element as discussed further hereafter.

Further, the portion of the redirected focusing beam 616 and the portion of the redirected measurement beam 654 may collectively form the same spatially separated illumination shape. In addition, both the portion of the redirected focusing beam 616 and the portion of the redirected measurement beam 654 are directed to the measurement module 650. By using an appropriate aperture device 668 whose aperture opening shape blocks or reflects the portion of the redirected focusing beam 616 (e.g., an opening having the shape of, e.g., FIG. 7B-D), the portion of the redirected focusing beam 616 is prevented from reaching the detector 678 in the measurement module 650. For example, the aperture device 668 may be a ring or plurality of off-axis openings with appropriate size so that the portion of the redirected focusing beam 616 is blocked completely while the portion of the redirected measurement beam 654 is not blocked. The aperture device 668 may be used with a beam shaping element as discussed further hereafter.

As will be appreciated, the aperture devices may be located in other parts of the beam paths. In an embodiment, an aperture device to block the measurement beam portion in, or for, the focusing module 610 may be located virtually anywhere in the path from the element 660 to the detectors 620, 622, other than in the path between the element 644 and the input 638. Desirably, the aperture devices 624 and 626 are used to block measurement radiation since they are used for the focus measurement. However, it may be desirable to provide an aperture opening for aperture devices 624, 625 that is not designed to block the measurement beam, in which case a further aperture device is provided to block the measurement radiation for the detectors 620, 622. Similarly, an additional aperture device may be used than aperture device 668 and similarly, the aperture device 668 may be located virtually anywhere in the path from the element 660 to the detector 678, other than in the path between the element 667 and the input 662.

In an embodiment, a beam shaping element 646 is provided in the optical path between the element 660 and the element 644. Thus, the beam shaping element 646 is, in this embodiment, both in the path of supply of radiation to the substrate 680 and the path of the return of radiation from substrate 680 toward detectors 620, 622. In an embodiment, the beam shaping element 646 is between the partially reflective optical element 644 and the reflective optical element 648. Further, for this embodiment, the focusing beam 612 will have an off-axis illumination shape, while the measurement beam 652 has an on-axis shape. As will be appreciated, the configuration could be reversed.

So, in this embodiment, the radiation from input 638 to the beam shaping element 646 has an on-axis shape (e.g., a circular shape provided directly by the input 638 or provided by, e.g., an aperture device between the input 638 and the element 646). The beam shaping element 646 then redirects that radiation to form an off-axis shape (e.g., a ring shape or a multipole arrangement). Therefore, the focusing beam 612 has an off-axis illumination shape for the substrate 680. Further, as discussed above, the measurement beam 652 has an on-axis illumination shape.

After the focusing beam 612 and the measurement beam 652 being incident on the substrate 680, the portion of the redirected focusing beam 614 and the portion of the redirected measurement beam 656 may collectively form a spatially separated illumination shape, for example, as shown in one of the illumination shapes in FIG. 11A-11D. In addition, both the portion of redirected focusing beam 614 and the portion of the redirected measurement beam 656 are directed to the focusing module 610, where the beam shaping element 646 converts the off-axis illumination shape of the portion of the redirected focusing beam 614 to an on-axis illumination shape, and converts the on-axis illumination shape of the portion of the redirected measurement beam 656 to an off-axis illumination shape. By using the first aperture device 620 and the second aperture device 622 whose aperture opening is similar to that in FIG. 7A, the portion of the redirected measurement beam 656 is prevented from reaching the detectors 620, 622 by the first and second aperture devices 620, 622, while the on-axis portion of redirected focusing beam 614 reaches the detectors 620, 622. Further, the portion of the redirected focusing beam 616 and the portion of the redirected measurement beam 654 may collectively form a same spatially separated illumination shape as discussed above. Both the portion of the redirected focusing beam 616 and the portion of the redirected measurement beam 654 are directed to the measurement module 650. By using the aperture device 668 whose aperture opening is similar to that in FIG. 8A, the portion of the redirected focusing beam 616 (which has an off-axis shape) is prevented from reaching the detector 678, while the portion of the redirected measurement beam 654 reaches the detector 678. In some examples, the aperture devices 620, 622, and/or 668 may be pinholes with suitable slit or opening sizes. In an embodiment, additionally or alternatively, a beam shaping element is provided in the optical path between the element 660 and the element 667 to as to change radiation shape of the measurement beam, e.g., at or near aperture device 668.

Additionally or alternatively, if the aperture device 668 is placed in the optical path between the partially reflective optical element 667 and the detector 678 (e.g., between the reflective optical element 672 and the lens 674), the first input 638 or the second input 662 alone may provide spatially separated beams of radiation as both the focusing beam and the measurement beam simultaneously. The rest of the setup 600 may be configured the same, or may be configured more simply by, e.g., if only the first input 638 is used, then input 662, lenses 664, 666 and element 667 may be eliminated or if only the second input 662 is used, then first input 638, lens 640, aperture stop 642 and element 644 may be eliminated. In an embodiment, the system 600 comprises a beam shaping element or an aperture device to create both the focusing beam and the spatially separated measurement beam at the same time from the radiation from the respective input 638, 662. In an embodiment, the input 638, 662 comprises a multi-core fiber or a fiber bundle operated in both illumination modes at the same time, where the inner core or fiber can provide the measurement beam and one or more outer cores or fibers can provide the focusing beam. In such an embodiment, the measurement beam and the focusing beam can relatively easily have different optical properties, e.g., different wavelength, different polarization, etc. For example, the illumination shape of the combined beam may be similar to FIGS. 11A-11D or any other suitable shapes, where the inner portion is the measurement beam and the outer portion is the focusing beam, or vice versa. The combined beam is redirected by the substrate 680 and directed back to the focusing module 610 and the measurement module 650 as described above.

Figure 12:
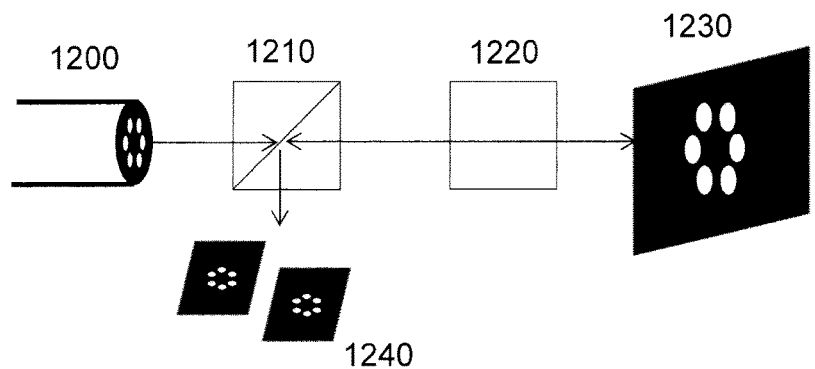
FIG. 12 schematically depicts an embodiment of a multi-core fiber in an illuminator of an inspection apparatus.
Figure 13:
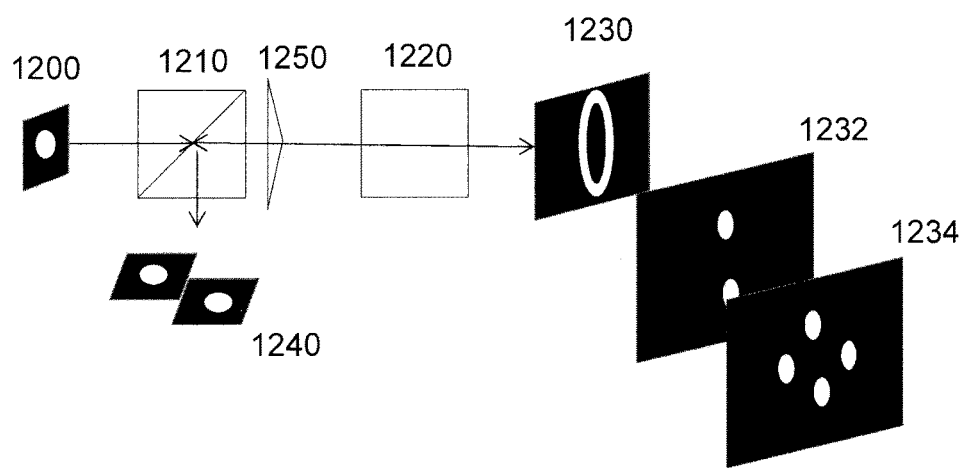
FIGS. 13 and 14 schematically depict embodiments of a beam shaping optical element comprising axicon lenses and/or prisms of an inspection apparatus.
Figure 14:
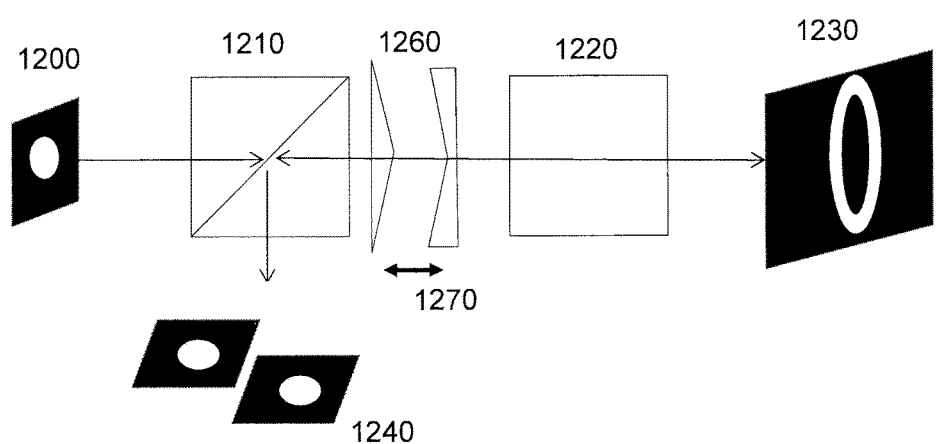

Example embodiments of simplified optical architectures of focus sensor systems are depicted in FIGS. 12, 13 and 14. Each system has an input field aperture 1200, optical module 1210 (including, e.g., beam splitter 632 in the focus detection branch as shown in FIG. 6), optical module 1220 (including, e.g., element 660 and objective 670 shown in FIG. 6), substrate 1230 (here shown as dark and illuminated with the bright focus spot(s)) and detector apertures 1240.

In the sensor system of FIG. 12, the input field aperture 1200 is in the form of a fiber bundle, which plays the role of an illumination aperture forming device. The detector apertures 1240 in FIG. 12 are shown as having the same layout as the illumination shape from input field aperture 1200, however it need not be identical in shape.

In the sensor system of FIG. 13, the input field aperture 1200 can be in the form of a plate having the opening shown (but as appreciated the input field aperture 1200 can be of different forms, including a fiber bundle, a SLM, etc., and the aperture can be of different shape or layout). FIG. 13 further comprises a beam shaping optical element 1250 positioned in the near pupil space (e.g., at position 640 in FIG. 6) to receive the radiation shaped according to the input field aperture 1200. FIG. 13 shows an example output illumination shape at the substrate for an axicon lens as the beam shaping optical element 1250 (the illumination shape shown on the substrate 1230 in FIG. 13), an example output illumination shape at the substrate for two wedges as the beam shaping optical element 1250 (the illumination shape shown on substrate 1232 in FIG. 13), and an example output illumination shape at the substrate for a pyramidal prism as the beam shaping optical element 1250 (the illumination shape shown on substrate 1234 in FIG. 13). As can be seen in FIG. 13, the illumination shape at the substrate is converted back to the input illumination shape for the detector apertures 1240. Thus, the input and output illumination shapes remain essentially the same even though the intermediate illumination shape at the substrate may be different. The detector apertures 1240 in FIG. 13 are shown as having the same layout as the illumination shape from input field aperture 1200, however it need not be identical in shape.

In the sensor system of FIG. 13, the input field aperture 1200 can be in the form of a plate having the opening shown (but as appreciated the input field aperture 1200 can be of different forms, including a fiber bundle, a SLM, etc., and the aperture can be of different shape or layout). FIG. 13 further comprises a beam shaping optical element 1260 positioned in the near pupil space (e.g., at position 640 in FIG. 6) to receive the radiation shaped according to the input field aperture 1200. In this example, the beam shaping optical element 1260 comprises a pair of axicons or prisms of which at least one axicon or prism is movable 1270 relative to the other axicon or prism. FIG. 14 shows an example output illumination shape at the substrate for a pair of axicon lenses as the beam shaping optical element 1250 (the illumination shape shown on the substrate 1230 in FIG. 14). As can be seen in FIG. 14, the illumination shape at the substrate is converted back to the input illumination shape for the detector apertures 1240. Thus, the input and output illumination shapes remain essentially the same even though the intermediate illumination shape at the substrate may be different. The detector apertures 1240 in FIG. 14 are shown as having the same layout as the illumination shape from input field aperture 1200, however it need not be identical in shape. Advantageously, in this embodiment, the beam shaping optical element 1260 has a capability of changing the radius of illumination shape at the substrate (e.g., radius of a ring, radial position of a plurality of spots, etc.) by merely changing the distance in the direction 1270 between the axicons or prisms.

In an embodiment, both the first input 638 and the second input 662 are laser sources. In an embodiment, the radiation beams emitted by the laser sources have a nominal wavelength and a relatively narrow bandwidth.

In an embodiment, there is provided a method comprising: directing a first measurement beam of radiation onto a substrate, the first measurement beam having a first intensity distribution; and directing a second focusing beam of radiation onto the substrate at a same time as the first measurement beam is directed onto the substrate, the second focusing beam-having a second intensity distribution, wherein at least part of the second intensity distribution is spatially separated from the first intensity distribution at least at the substrate and/or an aperture device.

In an embodiment, the at least part of the second intensity distribution comprises portions on opposite sides of the first intensity distribution. In an embodiment, the at least part of the second intensity distribution comprises a ring of radiation and/or a plurality of poles of radiation. In an embodiment, the method further comprises preventing at least a first portion of the first measurement beam redirected by the substrate and in an optical path toward a detector of the second focusing beam, from reaching the second focusing beam detector, while allowing at least a first portion of the second focusing beam redirected by the substrate to reach the second focusing beam detector. In an embodiment, preventing at least the first portion of the first measurement beam comprises blocking at least the first portion of the redirected first measurement beam using a first aperture device. In an embodiment, the method further comprises preventing at least a second portion of the second focusing beam redirected by the substrate and in an optical path toward a detector of the first measurement beam, from reaching the first measurement beam detector, while allowing at least a second portion of the first measurement beam redirected by the substrate to reach the first measurement beam detector. In an embodiment, preventing at least the second portion of the second focusing beam comprises blocking at least the second portion of the redirected second focusing beam using a second aperture device. In an embodiment, the first intensity distribution and/or the second intensity distribution is provided by an aperture device. In an embodiment, the first measurement beam and/or the second focusing beam is provided by a multi-core fiber or by a fiber bundle. In an embodiment, the first intensity distribution and/or the second intensity distribution is provided by a beam shaping optical element. In an embodiment, the beam shaping optical element comprises an axicon lens and/or a prism.

In an embodiment, there is provided an inspection apparatus comprising: a substrate holder configured to hold a substrate; an aperture device; and an optical system configured to direct a first measurement beam of radiation onto the substrate, the first measurement beam having a first intensity distribution, and configured to direct a second focusing beam of radiation onto the substrate at a same time as the first measurement beam is directed on the substrate, the second focusing beam having a second intensity distribution, wherein at least part of the second intensity distribution is spatially separated from the first intensity distribution at least at the substrate and/or the aperture device.

In an embodiment, the at least part of the second intensity distribution comprises portions on opposite sides of the first intensity distribution. In an embodiment, the at least part of the second intensity distribution comprises a ring of radiation and/or a plurality of poles of radiation. In an embodiment, the apparatus further comprises a detector of the second focusing beam and wherein the optical system is further configured to prevent at least a first portion of the first measurement beam redirected by the substrate and in an optical path toward the second focusing beam detector, from reaching the second focusing beam detector, while allowing at least a first portion of the second focusing beam redirected by the substrate to reach the second focusing beam detector. In an embodiment, the optical system is configured to block at least the first portion of the redirected first measurement beam using a first aperture device. In an embodiment, the apparatus further comprises a detector of the first measurement beam and wherein the optical system is further configured to prevent at least a second portion of the second focusing beam redirected by the substrate and in an optical path toward the first measurement beam detector, from reaching the first measurement beam detector, while allowing at least a second portion of the first measurement beam redirected by the substrate to reach the first measurement beam detector. In an embodiment, the optical system is configured to block at least the second portion of the redirected second focusing beam using a second aperture device. In an embodiment, the aperture device is configured to provide the first intensity distribution and/or the second intensity distribution. In an embodiment, the apparatus further comprises a multi-core fiber or a fiber bundle configured to provide the first measurement beam and/or the second focusing beam. In an embodiment, the apparatus further comprises a beam shaping optical element configured to provide the first intensity distribution and/or the second intensity distribution. In an embodiment, the beam shaping optical element comprises an axicon lens and/or a prism.

Embodiments have been described herein in relation to diffraction-based metrology, which, for example, measures the relative position of overlapping periodic structures from the intensity from the diffracted orders. However, embodiments herein may be applied, with appropriate modification where needed, to image-based metrology, which, for example, measures the relative position from target 1 in layer 1 to target 2 in layer 2 using high-quality images of the targets. Usually these targets are periodic structures or "boxes" (Box-in-Box (BiB)).

Although specific reference may have been made above to the use of embodiments in the context of metrology and optical lithography, it will be appreciated that embodiments may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method comprising:
   directing a first measurement beam of radiation onto a substrate, the first measurement beam having a first intensity distribution;
   directing a second focusing beam of radiation onto the substrate at a same time as the first measurement beam is directed onto the substrate, the second focusing beam having a second intensity distribution and at least part of the second intensity distribution is spatially separated from the first intensity distribution at least at the substrate and/or an aperture device;
   detecting at least part of the second focusing beam redirected by the substrate using a detector to produce a signal in response to detection of the at least part of the second focusing beam; and
   controlling a relative location between the substrate and an optical focus point of the first measurement beam based on the signal.

2. The method of claim 1, wherein the at least part of the second intensity distribution comprises portions on opposite sides of the first intensity distribution.

3. The method of claim 1, wherein the at least part of the second intensity distribution comprises a ring of radiation and/or a plurality of poles of radiation.

4. The method of claim 1, further comprising preventing at least a first portion of the first measurement beam redirected by the substrate and in an optical path toward the detector of the second focusing beam, from reaching the second focusing beam detector, while allowing at least a first portion of the second focusing beam redirected by the substrate to reach the second focusing beam detector.

5. The method of claim 4, wherein preventing at least the first portion of the first measurement beam comprises blocking at least the first portion of the redirected first measurement beam using a first aperture device.

6. The method of claim 1, further comprising preventing at least a second portion of the second focusing beam redirected by the substrate and in an optical path toward a detector of the first measurement beam, from reaching the first measurement beam detector, while allowing at least a second portion of the first measurement beam redirected by the substrate to reach the first measurement beam detector.

7. The method of claim 6, wherein the preventing at least the second portion of the second focusing beam comprises blocking at least the second portion of the redirected second focusing beam using a second aperture device.

8. The method of claim 1, wherein the first intensity distribution and/or the second intensity distribution is provided by an aperture device.

9. The method of claim 1, wherein the first measurement beam and/or the second focusing beam is provided by a multi-core fiber or by a fiber bundle.

10. The method of claim 1, wherein the first intensity distribution and/or the second intensity distribution is provided by a beam shaping optical element.

11. The method of claim 10, wherein the beam shaping optical element comprises an axicon lens and/or a prism.

12. An inspection apparatus comprising:
   a substrate holder configured to hold a substrate;
   an aperture device; and
   an optical system configured to direct a first measurement beam of radiation onto the substrate, the first measurement beam having a first intensity distribution, and configured to direct a second focusing beam of radiation onto the substrate at a same time as the first measurement beam is directed on the substrate, the second focusing beam having a second intensity distribution at least part of the second intensity distribution is spatially separated from the first intensity distribution at least at the substrate and/or the aperture device;
   a detector configured to detect at least part of the second focusing beam redirected by the substrate and to produce a signal responsive to detection of the at least part of the second focusing beam; and a control system configured to control a relative location between the substrate and an optical focus point of the first measurement beam based on the signal.

13. The apparatus of claim 12, wherein the at least part of the second intensity distribution comprises portions on opposite sides of the first intensity distribution.

14. The apparatus of claim 12, wherein the at least part of the second intensity distribution comprises a ring of radiation and/or a plurality of poles of radiation.

15. The apparatus of claim 12, wherein the optical system is further configured to prevent at least a first portion of the first measurement beam redirected by the substrate and in an optical path toward the second focusing beam detector, from reaching the second focusing beam detector, while allowing at least a first portion of the second focusing beam redirected by the substrate to reach the second focusing beam detector.

16. The apparatus of claim 15, wherein the optical system is configured to block at least the first portion of the redirected first measurement beam using a first aperture device.

17. The apparatus of claim 12, further comprising a detector of the first measurement beam and wherein the optical system is further configured to prevent at least a second portion of the second focusing beam redirected by the substrate and in an optical path toward the first measurement beam detector, from reaching the first measurement beam detector, while allowing at least a second portion of the first measurement beam redirected by the substrate to reach the first measurement beam detector.

18. The apparatus of claim 17, wherein the optical system is configured to block at least the second portion of the redirected second focusing beam using a second aperture device.

19. The apparatus of claim 12, wherein the aperture device is configured to provide the first intensity distribution and/or the second intensity distribution.

20. The apparatus of claim 12, further comprising a multi-core fiber or a fiber bundle configured to provide the first measurement beam and/or the second focusing beam.

21. The apparatus of claim 12, further comprising a beam shaping optical element configured to provide the first intensity distribution and/or the second intensity distribution.

22. The apparatus of claim 21, wherein the beam shaping optical element comprises an axicon lens and/or a prism.

* * * * *